(12) United States Patent
Browning et al.

(10) Patent No.: US 11,871,978 B2
(45) Date of Patent: Jan. 16, 2024

(54) PLASMA SCALPEL FOR SELECTIVE REMOVAL OF MICROBES AND MICROBIAL BIOFILMS

(71) Applicant: BOISE STATE UNIVERSITY, Boise, ID (US)

(72) Inventors: Jim Browning, Boise, ID (US); Ken Cornell, Boise, ID (US)

(73) Assignee: Boise State University, Boise, ID (US)

( * ) Notice: Subject to any disclaimer, the term of this patent is extended or adjusted under 35 U.S.C. 154(b) by 1467 days.

(21) Appl. No.: 15/956,895

(22) Filed: Apr. 19, 2018

(65) Prior Publication Data

US 2018/0303538 A1 Oct. 25, 2018

Related U.S. Application Data

(60) Provisional application No. 62/487,787, filed on Apr. 20, 2017.

(51) Int. Cl.
*A61B 18/04* (2006.01)
*H05H 1/24* (2006.01)
(Continued)

(52) U.S. Cl.
CPC ............... *A61B 18/042* (2013.01); *B60G 7/02* (2013.01); *B60T 1/06* (2013.01); *H05H 1/02* (2013.01); *H05H 1/2406* (2013.01); *H05H 1/46* (2013.01); *H05H 1/48* (2013.01); *A61B 34/30* (2016.02); *A61B 2017/00057* (2013.01); *A61B 2018/00291* (2013.01); *A61B 2018/00452* (2013.01); *A61B 2018/00583* (2013.01);
(Continued)

(58) Field of Classification Search
CPC .......... A61B 2018/00583; A61B 2018/00642; A61B 2218/007
See application file for complete search history.

(56) References Cited

U.S. PATENT DOCUMENTS 6,374,158 B1 * 4/2002 Fusaro, Jr. ........... B23K 10/027
                                                                318/568.14
6,478,875 B1 * 11/2002 Sampath ................ C23C 24/04
                                                                118/712
(Continued)

FOREIGN PATENT DOCUMENTS

WO    2015059702 A1    4/2015
WO    2015071099 A1    5/2015

OTHER PUBLICATIONS

Ghasemi ["Interaction of multiple plasma plumes in an atmospheric pressure plasma jet array", J. Phys. D: Appl. Phys. 46 (2013)]. (Year: 2013).*

(Continued)

*Primary Examiner* — Oommen Jacob
(74) *Attorney, Agent, or Firm* — McKee, Voorhees & Sease, PLC

(57) ABSTRACT

The disclosure relates to the medical device field. In particular, the disclosure relates to a dynamically controlled plasma scalpel in combination with an imaging system to selectively remove biofilm while minimizing damage to healthy tissue. Systems and apparatuses according to the disclosure include: (1) dynamically controlled plasma scalpel, (2) biofilm imaging system, (3) computer control system, (4) three-dimensional scalpel positioning stage, and (5) biofilm detritus removal system.

19 Claims, 7 Drawing Sheets

(51) Int. Cl.
| | |
|---|---|
| *H05H 1/02* | (2006.01) |
| *H05H 1/48* | (2006.01) |
| *H05H 1/46* | (2006.01) |
| *B60G 7/02* | (2006.01) |
| *B60T 1/06* | (2006.01) |
| *A61N 1/40* | (2006.01) |
| *A61L 2/14* | (2006.01) |
| *A61B 90/00* | (2016.01) |
| *A61B 18/00* | (2006.01) |
| *B60B 27/02* | (2006.01) |
| *B62D 7/18* | (2006.01) |
| *A61B 34/30* | (2016.01) |
| *A61B 17/00* | (2006.01) |

(52) U.S. Cl.
CPC .............. *A61B 2018/00642* (2013.01); *A61B 2018/00738* (2013.01); *A61B 2090/373* (2016.02); *A61B 2090/3735* (2016.02); *A61B 2090/395* (2016.02); *A61B 2090/3933* (2016.02); *A61B 2218/007* (2013.01); *A61L 2/14* (2013.01); *A61N 1/40* (2013.01); *B60B 27/02* (2013.01); *B60G 2204/418* (2013.01); *B60G 2206/50* (2013.01); *B62D 7/18* (2013.01); *H05H 1/466* (2021.05); *H05H 1/475* (2021.05); *H05H 2245/34* (2021.05)

(56) References Cited

U.S. PATENT DOCUMENTS

| | | | | |
|---|---|---|---|---|
| 7,338,482 | B2* | 3/2008 | Lockwood | A61M 27/00 604/326 |
| 8,764,701 | B1* | 7/2014 | Hicks | A61B 18/042 604/23 |
| 9,254,167 | B2 | 2/2016 | Davison et al. | |
| 9,269,544 | B2* | 2/2016 | Koo | H05H 1/2406 |
| 9,314,603 | B2 | 4/2016 | Kummerfeld et al. | |
| 9,550,007 | B2 | 1/2017 | Tsai et al. | |
| 9,555,145 | B2* | 1/2017 | Ward | A61L 2/14 |
| 9,855,441 | B2* | 1/2018 | Liao | A61N 1/44 |
| 2004/0230186 | A1* | 11/2004 | Obrebski | A61B 34/32 606/39 |
| 2006/0156983 | A1 | 7/2006 | Penelon et al. | |
| 2006/0275847 | A1* | 12/2006 | Goodyer | G02B 21/008 435/25 |
| 2007/0029500 | A1* | 2/2007 | Coulombe | H01T 23/00 250/423 F |
| 2010/0160838 | A1* | 6/2010 | Krespi | A61B 18/26 604/20 |
| 2011/0160069 | A1* | 6/2011 | Corrie | G01N 33/54366 427/256 |
| 2012/0197344 | A1* | 8/2012 | Taft | A61B 18/148 607/51 |
| 2013/0026137 | A1 | 1/2013 | Kindel et al. | |
| 2013/0199540 | A1* | 8/2013 | Buske | H05H 1/42 128/845 |
| 2013/0226073 | A1* | 8/2013 | Kummerfeld | A61L 2/14 604/23 |
| 2013/0261536 | A1* | 10/2013 | Sartor | A61B 18/042 604/23 |
| 2014/0074068 | A1* | 3/2014 | Olmstead | G01N 21/4795 604/522 |
| 2014/0276784 | A1* | 9/2014 | Ward | A61L 2/14 606/41 |
| 2014/0378892 | A1 | 12/2014 | Keidar et al. | |
| 2016/0138006 | A1* | 5/2016 | Canady | A61B 18/042 606/34 |
| 2016/0198994 | A1* | 7/2016 | Murphy | A61B 5/486 600/477 |
| 2016/0287310 | A1 | 10/2016 | Nettesheim et al. | |
| 2016/0295676 | A1 | 10/2016 | Patelli et al. | |
| 2018/0303538 | A1* | 10/2018 | Browning | H05H 1/34 |
| 2019/0380779 | A1* | 12/2019 | Negus | A61B 18/203 |

OTHER PUBLICATIONS

Mohmmed [A novel experimental approach to investigate the effect of different agitation methods using sodium hypochlorite as an irrigant on the rate of bacterial biofilm removal from the wall of a simulated root canal model, Dental Materials 32 (2016) 1289-1300]. (Year: 2016).*

Hoffman et al., "Cold Atmospheric Plasma: methods of production and application in dentistry and oncology", Medical Gas Research, vol. 3, No. 21, 15 pages, 2013.

Maisch et al., "Contact-Free Inactivation of Candida albicans Biofilms by Cold Atmospheric Air Plasma", Applied and Environmental Microbiology, vol. 78, No. 12, pp. 4242-4247, Jun. 2012.

Ermolaeva et al., "Bactericidal effects of non-thermal argon plasma in vitro, in biofilms and in the animal model of Infected wounds", Journal of Medical Microbiology, vol. 60, pp. 75-83, 2011.

"Supporting your manufacturing needs with game changing plasma technology", http://www.surfxtechnologies.com, Surfx, access by Applicant Sep. 25, 2018.

* cited by examiner

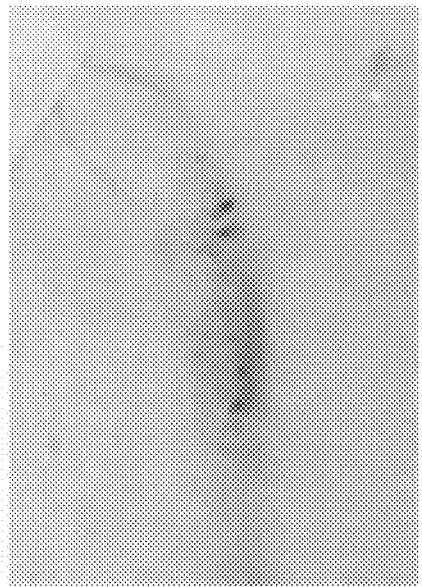 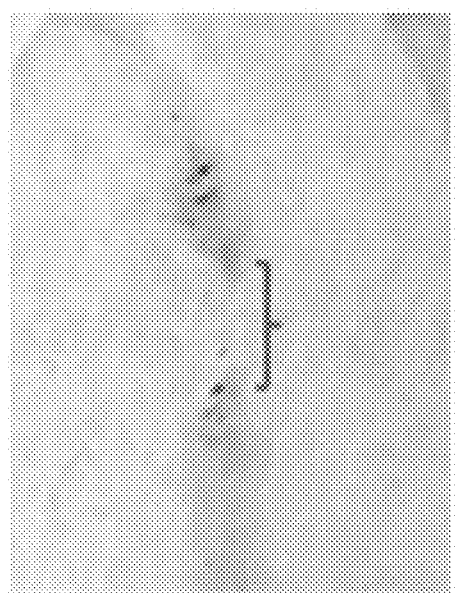
*FIG. 2A*  *FIG. 2B*
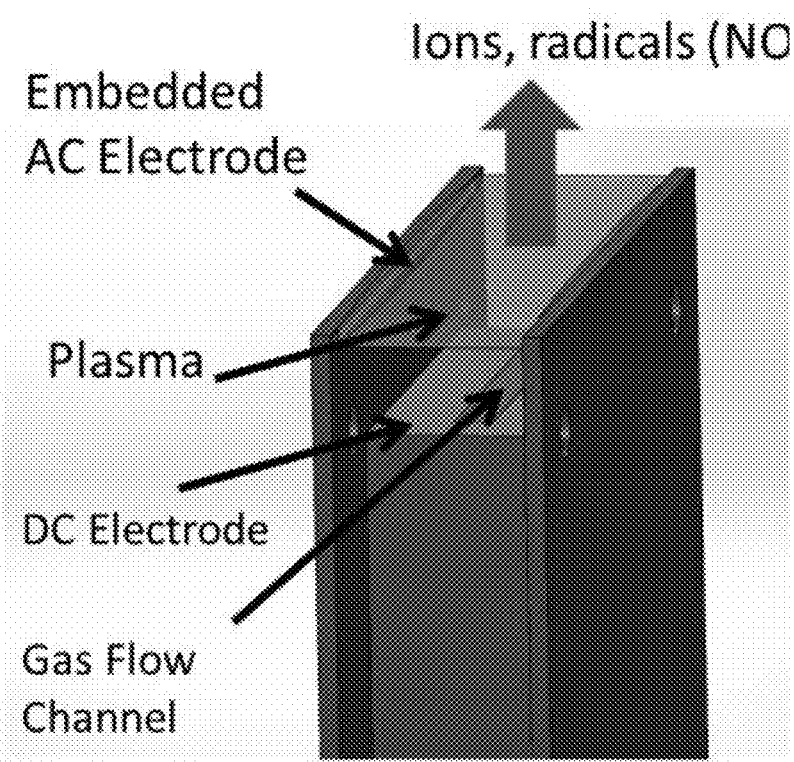
*FIG. 3*

PLASMA SCALPEL FOR SELECTIVE REMOVAL OF MICROBES AND MICROBIAL BIOFILMS

CROSS REFERENCE TO RELATED APPLICATION

This application claims priority under 35 U.S.C. § 119 to provisional application Ser. No. 62/487,787 filed Apr. 20, 2017, titled "PLASMA SCALPEL FOR SELECTIVE REMOVAL OF MICROBES AND MICROBIAL BIOFILMS," herein incorporated by reference in its entirety including, without limitation, the specification, claims, and abstract, as well as any figures, tables, or drawings thereof.

GRANT REFERENCE

This invention was made with government support under the National Institute of General Medical Sciences of the National Institutes of Health research grants P20GM103408 and P20GM109095. The government has certain rights in the invention.

FIELD OF THE DISCLOSURE

The disclosure relates to the medical device field. In particular, the disclosure relates to a dynamically controlled plasma scalpel in combination with an imaging system to selectively remove biofilm while minimizing damage to healthy tissue. Ultimately, the disclosure leads to the development of simple, cost-effective technology to debride wounds and enhance wound healing by decreasing the wound bioburden.

BACKGROUND OF THE DISCLOSURE

Biofilms are difficult to remove and constitute a major impediment to healing of chronic wounds and burns. This is particularly true in aging populations where complications from these wounds exact a significant toll in terms of patient suffering and financial cost. Reports estimate that chronic wounds account for $10-25B in annual healthcare costs. Wound debridement to remove foreign material and dead and infected tissue is recognized as a critical step in sponsoring wound closure. Current wound debriding practices include sharp debridement, hydrosurgery, and topical therapies to remove necrotic tissues and associated biofilms. The sharp debridement method (scrubbing) is the reference standard, but it is painful and damages healthy tissue while failing to completelybiofilm. Hydrosurgery is useful for removing necrotic tissue but may also aerosolize bacterial contaminants and disperse them in the wound. Topical treatments (nanoparticles, antiseptics, honey, etc.) are useful in some wounds, but they may also be poorly penetrating into biofilms, have only short-term effects, or exert toxicities to host tissue.

More recently cold atmospheric pressure plasma (CAP) treatment methods have been developed for removing biofilm, but these methods need substantial improvements for effective deployment, including selectivity between healthy tissue and biofilms. Development of a practical, flexible, and low-cost biofilm debridement procedure could provide major improvements in healthcare.

Accordingly, it is an objective of the disclosure to develop a plasma scalpel system to image and dynamically remove biofilms.

A further object of the disclosure is to develop a plasma scalpel system which selectively removes biofilms from wounds.

Accordingly, it is an objective of the disclosure to develop a dynamically controlled plasma scalpel in which the biofilm etch rate can be varied in real time using the system operating parameters, and the device can be moved in three directions and a variety of angles with high spatial precision (<100 um) to etch the biofilm at a specific location.

Accordingly, it is an objective of the disclosure to develop a biofilm imaging approach in which the biofilm in the wound is stained so that it can be imaged, and then image analysis is used to control the plasma scalpel position and etch rate to debride only biofilm, necrotic tissue, and bacteria.

Accordingly, it is an objective of the disclosure to develop a detritus removal system to remove bacteria and biofilm byproducts destroyed by the plasma scalpel system to ensure it does not remain within the wounds.

Other objects, advantages and features of the present disclosure will become apparent from the following specification taken in conjunction with the accompanying figures.

BRIEF SUMMARY OF THE DISCLOSURE

The disclosure contributes to the field by producing a device with tunable parameters that ultimately demonstrate selective ablation of biofilms, while leaving normal healthy wound tissue unharmed. This contribution is expected to be significant because wound biofilms are one of the major factors that delay or prevent proper healing, and current wound debridement protocols are painful, toxic, or unselective in their effects and, thus, need improvement. Ultimately, the plasma scalpel apparatus and system as well as methods of use for wound debridement according to the disclosure could help solve the problem of poor wound resolution and >$10 B healthcare cost of annual chronic wound treatment.

In an aspect of the disclosure, a dynamically controlled plasma scalpel to selectively ablate biofilms and necrotic tissues from wounds is provided. Plasma medicine is an exciting and rapidly emerging field, and in an aspect of the disclosure, the dynamically controllable delivery of ionic gas molecules to selectively etch undesired material from a wound site is provided. In a preferred aspect, CAP plasma with oxygen can be used to remove biofilm by both physical (sputter) and chemical means. In plasma processing, the physical bombardment of a surface by energetic particles (50-150 eV) can be used to knock off the surface material in a process called "sputtering." Reactive species can also be used to chemically interact with surface material to remove the material through chemical "etching." This type of "reactive ion etch" can be actively controlled to remove biofilm at a varying rate. Thus, the plasma approach of the disclosure offers unique biological, physical, and chemical means to debride wounds. It is an aspect of the disclosure to combine a dynamically controlled plasma source (scalpel) in combination with a biofilm imaging system to debride the wound by selectively etching only the biofilm and stopping on healthy tissue.

In an aspect, the disclosure is a plasma scalpel system comprising: a dynamically controlled plasma scalpel; a biofilm imaging system; a computer control system; a three-dimensional scalpel positioning stage; and a biofilm detritus removal system.

In a further aspect, the disclosure provides methods of treating wounds comprising: providing the plasma scalpel system comprising a dynamically controlled plasma scalpel;

a biofilm imaging system; a computer control system; a three-dimensional scalpel positioning stage; and a biofilm detritus removal system; and debriding the wound using the plasma scalpel system.

In a still further aspect, the disclosure is a method of selectively removing biofilm by identifying and staining the biofilm; employing the plasma scalpel system according to the disclosure; and removing the biofilm.

While multiple embodiments are disclosed, still other embodiments of the present disclosure will become apparent to those skilled in the art from the following detailed description, which shows and describes illustrative embodiments of the disclosure. Accordingly, the figures and detailed description are to be regarded as illustrative in nature and not restrictive.

BRIEF DESCRIPTION OF THE FIGURES

FIGS. 2A-2B show *Staph. aureus* biofilm etch results showing images of a stained biofilm on a coverslip (FIG. 2B), the biofilm after a 600 s etch with the plasma source according to the disclosure (FIG. 2A). The bracket indicates the channel etched by the plasma scalpel perpendicular to the line of the biofilm. Note that a white fabric is placed under the glass for image contrast.

FIG. 3 shows a single channel view of plasma discharge concept according to the disclosure. The glow discharge channel is typically <1 mm wide. Embedded AC electrodes generate the plasma and the DC electrode accelerates ions and radicals out of the channel. Gas flows through a slot in the DC electrode.

Figure 1A:
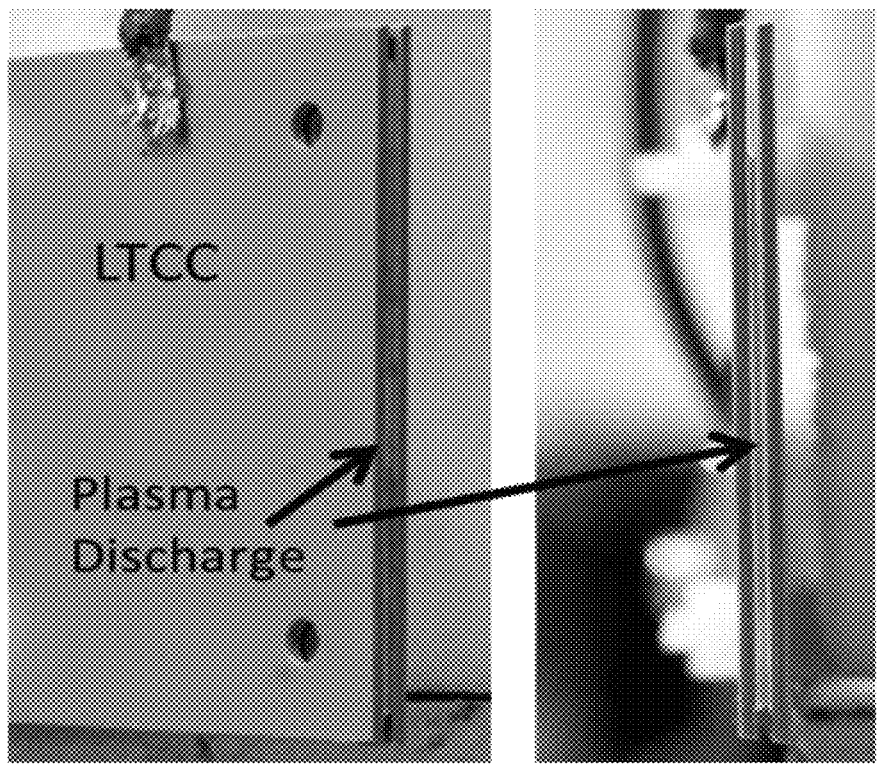
FIG. 1A shows a photograph of 4 cm×4 cm device showing a front and edge view of the structure with a plasma discharge in the trench and FIG. 1B shows a photograph of four discharges running together.

Various embodiments of the present disclosure will be described in detail with reference to the figures, wherein like reference numerals represent like parts throughout the several views. Reference to various embodiments does not limit the scope of the disclosure. Figures represented herein are not limitations to the various embodiments according to the disclosure and are presented for exemplary illustration of the disclosure.

DETAILED DESCRIPTION OF THE PREFERRED EMBODIMENT

The embodiments of this disclosure are not limited to particular embodiments, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Definitions

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and systems of the present disclosure may comprise, consist essentially of, or consist of the components and ingredients of the present disclosure as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Overview

A variety of treatments exist for chronic wounds, including the use of topical and systemic antibiotics and antiseptics, growth-factor and nitric oxide releasing polymers, and hyperbaric oxygen chamber therapy. Wound debridement to remove necrotic and infected tissue is recognized as an essential step in wound care to sponsor satisfactory resolution. However, the current treatments (sharp debridement, hydrosurgery, topicals, etc.) have limitations that prevent their success in many wounds. Therefore, new techniques and improved understanding of those approaches are needed. Plasma gas treatments are relatively new and offer many unique benefits to the delivery of therapeutic molecules to the wound site.

To develop a wound imaging and plasma debriding device according to the disclosure, biofilms on glass coverslips are stained to identify necrotic tissues and biofilms and imaged using a visible light source and camera. The disclosure includes demonstration of the removal of Staph. aureus and Ps. aeruginosa biofilms (chosen for their importance as wound pathogens) as a function the plasma scalpel operating time. In general, the plasma operating parameters (AC power, ion energy, gas flow rate, gas mixture) can be varied to adjust the removal rate.

The disclosure is based on the understanding that plasma species from a CAP can be used to etch or sputter, or debride, biofilm. However, the selectivity to healthy tissue, the understanding of the plasma-tissue interface, and the control of the CAP for use in real-world treatment settings are critical issues resolved by the system, apparatus, and methods of the disclosure. The disclosure uses a dynamically controlled plasma system that generates and delivers plasma species only to the biofilm, and then uses the dynamic control to stop or slow the etching when healthy tissue is exposed. The ability of the system, apparatus, and methods of the disclosure to accurately image and measure the location of biofilm in the wound allows for debridement only where needed. This selective approach greatly enhances the wound debridement capabilities of CAP to improve healing.

The disclosure improves upon existing capacitively-coupled, atmospheric pressure, plasma source as the plasma scalpel. A diagram of the plasma scalpel source is shown in FIG. 3. In an embodiment of the disclosure, the scalpel is <2 mm wide. The scalpel consists of several components: a mechanical structure containing electrodes and gas feed channels, AC capacitive discharge electrodes, and DC discharge electrodes. The structure material is a Low Temperature Co-fired Ceramic (LTCC) which is robust to plasma bombardment and can be heated to very high temperatures (>400 C) if necessary. The LTCC structures can be fabricated in a variety of geometries and layouts for low cost. The system allows generation of cold plasma at atmospheric pressures using a mixture of argon and oxygen, air, or nitrogen. The plasma is generated using a low frequency (20 kHz), capacitive discharge in combination with Direct Current (DC) glow discharge for ion acceleration. This is one type of plasma source that could be used in the plasma scalpel system. Any suitable plasma source which removes biofilms may be employed in the systems, apparatuses, and methods according to the disclosure.

Figure 1B:
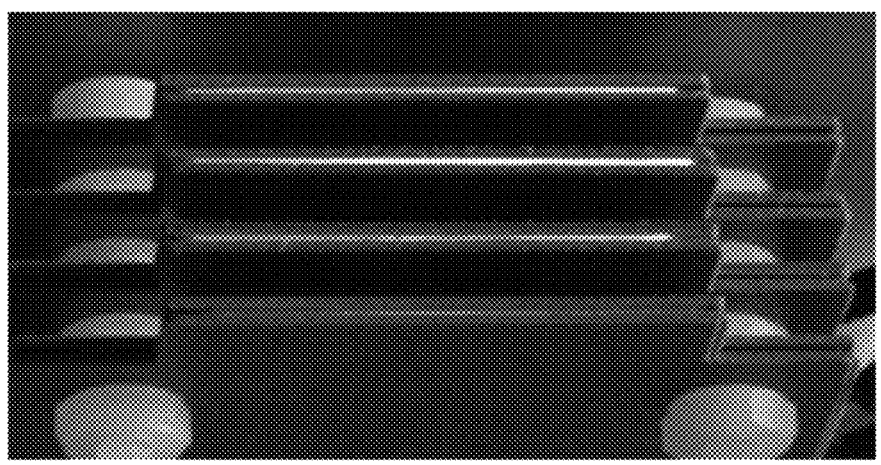

Applicants have demonstrated atmospheric pressure, capacitive discharges in air and with argon using various plasma device configurations. These devices are fabricated using a Low Temperature Co-fired Ceramic (LTCC) material. One example is shown in FIG. 1 where a 20 kHz, 5 kV signal is applied between two electrodes buried within an LTCC layer with a 0.7 mm wide trench. The capacitive discharge can be seen across the gap. Not pictured is a DC electrode located below the discharge. While a plasma debriding device would be much narrower, the structure according to the disclosure has been used to show that a DC glow discharge can be initiated using the AC and DC electrodes and that ions from the discharge can be accelerated away from the plasma to a collector plate (not shown) which represents a wound site.

Applicants have also conducted experiments to demonstrate that the plasma device can ablate or etch biofilms grown on glass. In this experiment, glass coverslips were partially submerged for 48 hr in cultures of *Staphylococcus aureus* (ATCC 25923). The coverslips were then rinsed to remove loosely bound cells, and the biofilm was lightly stained with 0.2% Trypan blue for 5 min (FIGS. 2A-2B). The heaviest biofilm staining was seen at the air-liquid interface on the coverslip. The biofilm is clearly thicker in some regions from the immersion process as evidenced by a darker stain. The stained biofilm was then debrided (etched) using our plasma scalpel for 600 s to ensure much of the biofilm was cleared. The scalpel was aligned perpendicular to the direction of the biofilm. As seen in FIG. 2A, after etching a strip of biofilm has been removed by the plasma scalpel. This preliminary result demonstrates our basic premise: the plasma scalpel can debride stained biofilm.

A desirable feature of a practical, deployed plasma scalpel system would be low cost, around $35 k-$40 k. Such a system would be easily deployable to any treatment facility (particularly rural areas) and require only moderate training to operate as most of the system could be automated. Variations in the system would use different arrays of plasma scalpels for large versus small wounds. Treatment times would be preferably less than about 60 minutes, more preferably less than about 45 minutes, and more preferably less than about 30 minutes based on biofilm etch rates. Thicker biofilms or larger areas might require arrays of scalpels initially to speed biofilm removal. In an embodiment of the disclosure, these arrays of scalpels would still fit into one system. The scalpels would be attached and detached as replaceable heads. Note that the plasma source is easily cleaned as it can withstand high temperatures (>400° C.) for autoclave, but the cameras/fiber optics and light sources might need be covered to protect them from contamination.

Figure 4:
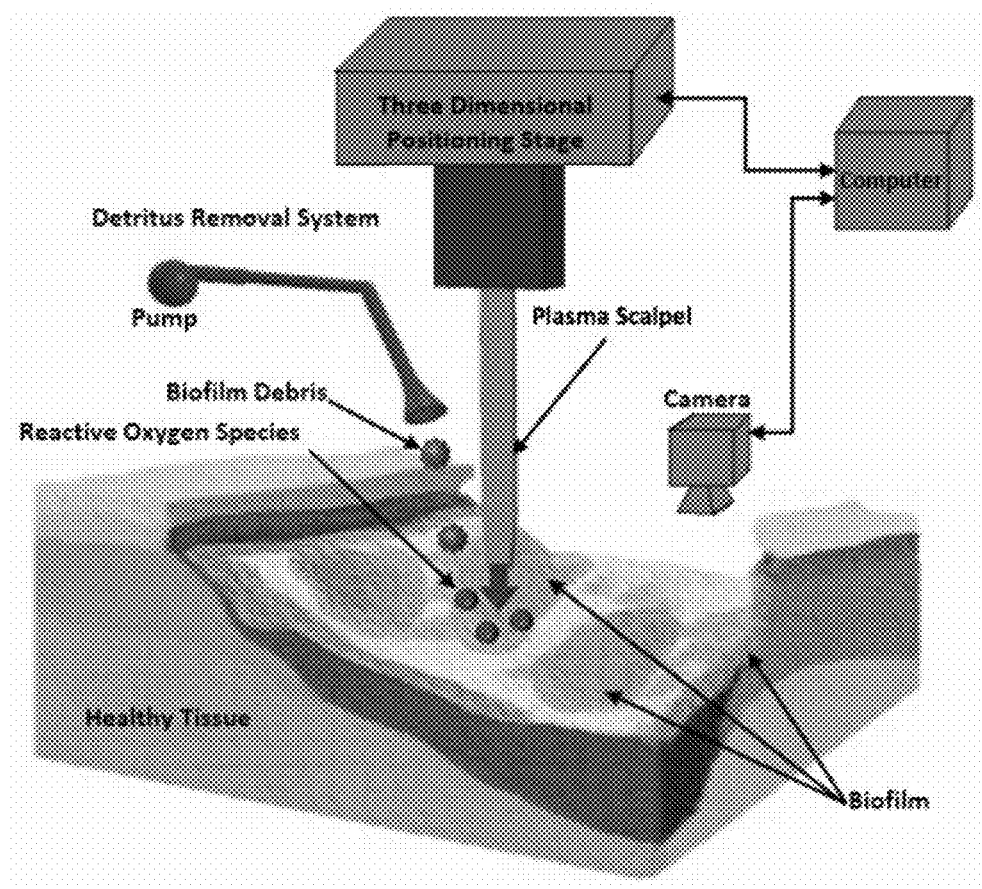
FIG. 4 shows the plasma wound healing device concept according to the disclosure: a plasma scalpel is moved on a three-dimensional positioning stage to debride biofilm. An imaging system captures the stained biofilm for analysis, and a computer control system adjusts both the plasma scalpel position over the biofilm and etch rate so only biofilm is debrided. A detritus removal system exhausts the biofilm, gases, and other material. An array of scalpels could be used.
Figure 5:
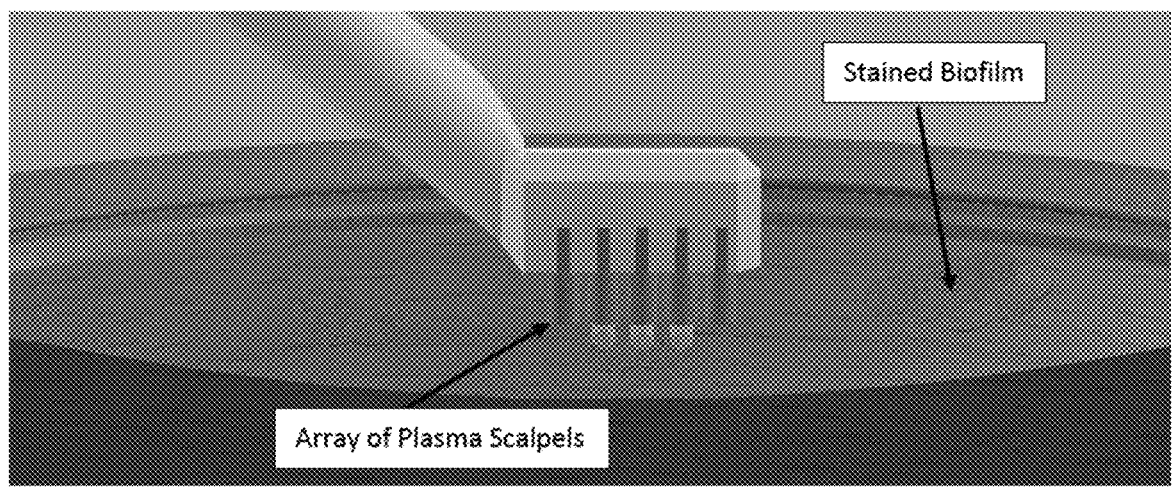
FIG. 5 shows an array of scalpels being used to selectively remove biofilm where each plasma scalpel can be independently controlled to vary the plasma at each location and control the plasma etch rate as needed.

A representation of the plasma scalpel system according to the disclosure is shown in FIG. 4 as it might be implemented for actual biofilm debriding. The overall system could be used to treat small (<2 mm) or large (20 cm) wounds. As shown in FIG. 4, the concept has five major components: (1) dynamically controlled plasma scalpel, (2)

biofilm imaging system, (3) computer control system, (4) three-dimensional scalpel positioning stage, and (5) biofilm detritus removal system. These components are described here.

Dynamically Controlled Plasma Scalpel

Figure 6:
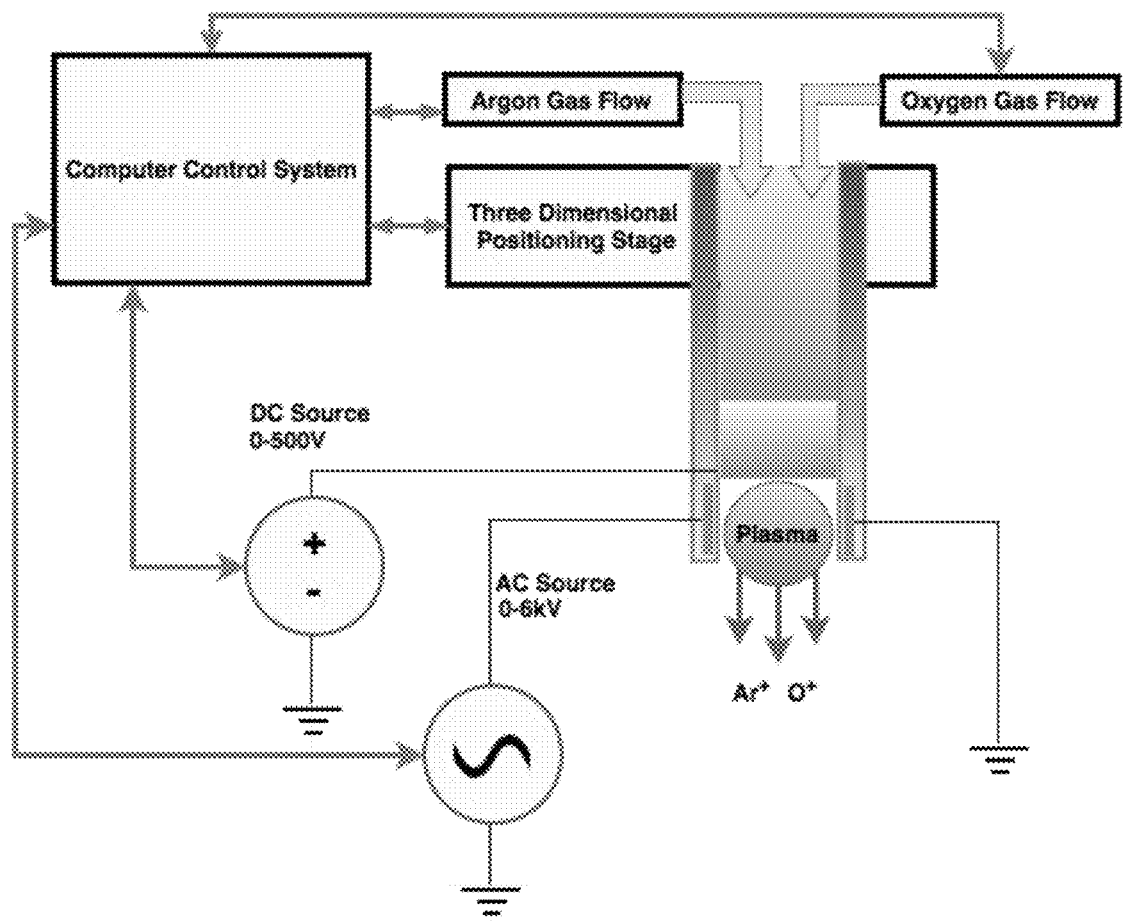
FIG. 6 shows the dynamically controlled plasma scalpel components including the variable AC and DC power supplies, the argon and oxygen gas flow controllers, and the positioning stage, and computer control system.
Figure 7:
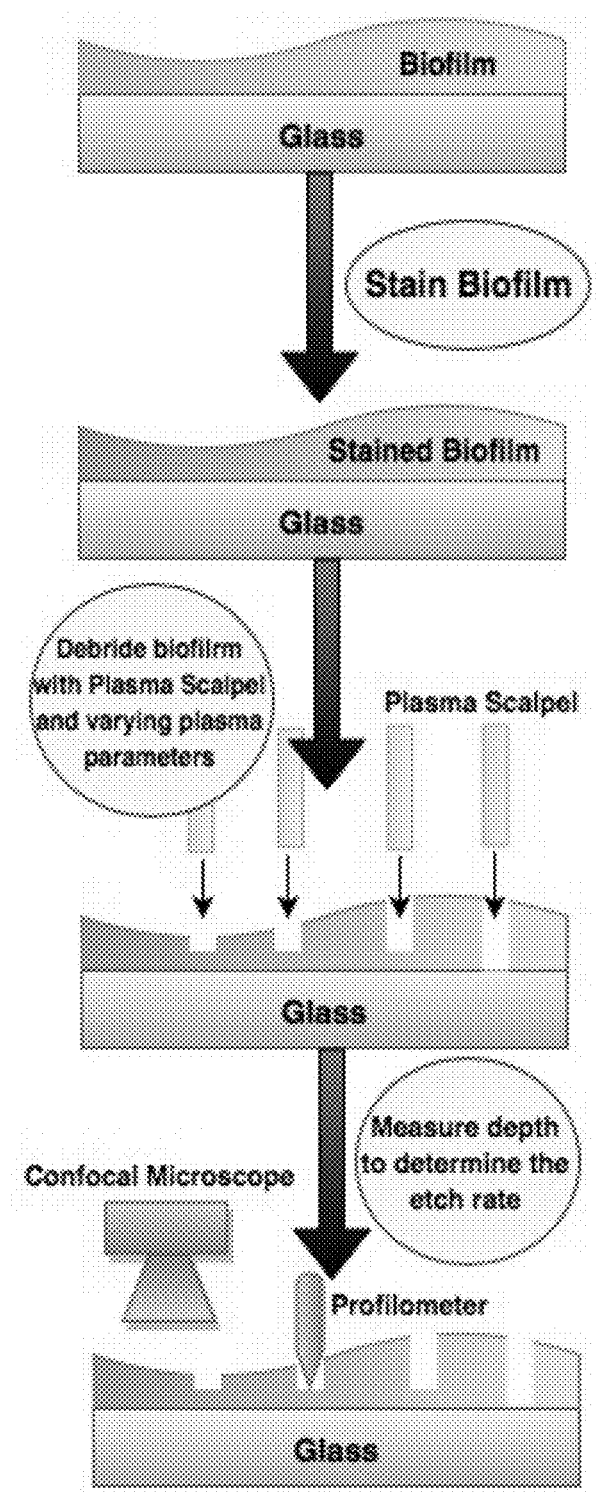
FIG. 7 shows the plasma etch rate experimental set up showing the four major process steps of biofilm growth, biofilm staining, biofilm etching, and etch rate measurement used to obtain the preliminary data.

The plasma discharge is formed using at least two insulated (covered) electrodes spaced horizontally apart as in FIG. 3. In an embodiment of the disclosure, the electrodes may be in any suitable configuration which provides for removal of biofilm. For example, the electrodes may be arranged in a cylindrical, rectangular, or any other suitable configuration. Further, a combination of electrodes from different sources may be employed. In an embodiment, the capacitive discharge forms a low temperature, reservoir plasma facing the treatment site. This reservoir plasma is used to dissociate the working gases into oxygen species using argon to form the plasma. Other gases could be used such as air or nitrogen as the working gas. The electrode spacing can be from about 0.001 to about 1 cm, preferably from about 0.01 to about 0.5 cm, and more preferably from about 0.01 cm to about 0.01 cm depending upon the approach. Instead, the bombardment of reactive species and high energy (10-150 eV) ions and neutral gas particles are used to remove biofilm. There are both passive (electrode spacing, DC electrode area, channel diameter, and/or combinations thereof) and active (gas ratio, gas flow rate, capacitive discharge power, DC electrode voltage, scalpel to wound distance, and/or combinations thereof) control features. In an additional embodiment of the disclosure, relative bias, angle of incidence, three-dimensional positioning stage, multidimensional positioning stage, and/or combinations thereof are also control features. A schematic representation of these various controls used to dynamically adjust an individual scalpel is shown in FIG. 6. In an embodiment, these control features may be applied to multiple scalpels within a single system. These control features can be varied in order control the biofilm etch rate. Because of the rapid control of these variables, the plasma source can be dynamically controlled in real-time, with a response time on the order of milliseconds, preferably less than 500 milliseconds, preferably less than 250 milliseconds, and more preferably less than 100 milliseconds to vary the etch rate as needed. This approach would then allow the biofilm removal rate to slow as healthy tissue is exposed, thereby reducing harm to healthy tissue. Hence, when the biofilm is thick, the etch rate can be fast, but as the biofilm thins, the rate can be slowed. The system includes computer-controlled AC and DC power supplies and two gas flow controllers (FIG. 6). It should be noted that while only a single, narrow plasma scalpel is shown in FIG. 6, multiple scalpels or an array of scalpels might be used to enhance the biofilm debridement rate over a large area as shown in FIG. 4. According to this embodiment, the scalpels can be turned on and off as needed with variable etch rates. In this manner the treatment time is decreased as multiple plasma scalpels are used simultaneously with active control to remove only biofilm and not healthy tissues by adjusting each scalpel independently based on imaging of the biofilm. When narrow and deep wounds are encountered, the single scalpel may be used to move closer into the wound to debride the biofilm.

Biofilm Imaging System

In order to use the dynamic control capabilities of the plasma scalpel and to provide the required selectivity between biofilm and healthy tissue, the biofilm must be imaged. According to the present disclosure, this imaging is accomplished by biofilm and necrotic tissue staining with Trypan Blue. Other staining techniques to provide selectivity with healthy tissue are possible including, for example, Spyro Ruby, Acridine orange, Toliding blue, Alcian blue, and Congo red are some examples. After the stain is dispensed, the wound is flushed or wiped to remove excess stain. Irrigation is normally performed with sterile saline (0.8% NaCl in water). Eschar, necrotic and granulomatous tissue and biofilms remain stained, while normal tissue loses color. The wound site is then illuminated with visible light, and a camera or fiber optic system with high resolution and the necessary magnification is set to provide a real-time image of the stained material on the wound. This camera or fiber optic might move with the plasma scalpel or be a separate system. The camera can be at an angle relative to the illumination to provide a level of 3D imaging. Multiple light sources or cameras could be used to enhance the 3D image capability. The image will provide the spatial location of the biofilm to the computer control system for dynamic activation of the plasma scalpel. The ultimate capability of the method will need to be determined as to the ability to measure the relative thickness of the biofilm for system control. The motion of the scalpel can be slow enough that normal camera frame rates (approximately about 50 fps) can be used; however higher speed cameras (approximately from about 100 to about 1000 fps) might also be used to provide greater dynamic control. However, the real-time imaging capability according to the disclosure is fast enough to slow or stop the plasma scalpel as the healthy tissue is exposed. According to an embodiment of the present disclosure, a long-distance microscope and camera for the system may beused. The magnified imaging is required to resolve the biofilm for image analysis.

Other examples would be to use other systems to "image" the biofilm and wound including concepts such as Scanning Laser Tomography (SLOT) to map both the wound and the biofilm locations.

Three Dimensional Scalpel Positioning System

In an embodiment, the plasma scalpel will have the capability of moving in three-dimensions and at a variety of angles relative to the wound. A positioning stage or robotic arm using computer driven, high resolution stepping motors may be employed to provide precise positioning. In such an embodiment, approximately about a 100 μm resolution is needed; however in an alternative embodiment, resolution could range from about 0.01 to about 1 mm depending upon application. Based on the image processing, the stage will position the scalpel from about 0.01 mm to about 20 mm, preferably from about 0.1 mm to about 15 mm, and more preferably from about 0.1 mm to about 10 mm, and even more preferably less than 5 mm above the biofilm and move the scalpel as needed to debride the wound. In one embodiment of the method, the scalpel could remain at one location until the biofilm is entirely removed at that location as indicated by imaging. In an alternative embodiment, the scalpel could be moved back and forth (raster) to remove the biofilm over a large area so that deep trenches are not created which would limit imaging. As the scalpel tracks back and forth across the wound debriding the biofilm, much like mechanical milling, the imaging system updates the biofilm locations and estimates the remaining thickness. Hence, the system and methods of the disclosure act to remove the thickest biofilm first and then slowly lower down as the biofilm thins.

Biofilm Detritus Removal System

The final component of the apparatus and system according to the disclosure is the detritus removal system. The detritus removal system may be a slightly negative pressure (vacuum) tube adjacent to the plasma source. In such an embodiment, as the biofilm is removed and lifts from the surface, the negative pressure of the tube directs this material away. This removal system also removes any plasma gases and biological materials from the wound area as well. While the removal system is shown in FIG. 4 as a small tube near the plasma source, in alternative embodiment, the entire wound area could be enclosed in a flexible chamber with cushions that rest against the body to provide a limited seal. A surrounding structure (outer exhaust chamber) can be used to differentially pump the region between the wound and the pump exhaust. Hence, the feed gas flows through channels into the plasma generation region and then to the wound site. This approach protects the patient and operators from these gases and byproducts such as the removed bacteria and ozone. Hence, the optimum mixture of gases can be used rather than atmospheric pressure air.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1: Etching of Biofilms

Figure 8A:
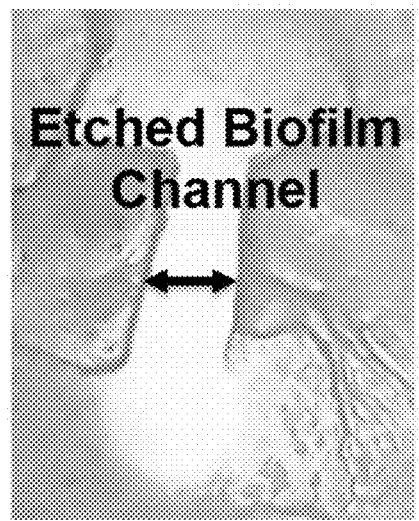
FIG. 8A shows a channel etched in the biofilm at high magnification to demonstrate biofilm removal to the glass substrate and FIG. 8B shows the reduction in the concentration of Colony Forming Units (CFUs) when all biofilm is treated with plasma on a coverslip. The reduction versus plasma exposure time demonstrates that the plasma is killing biofilm with sufficient exposure time.
Figure 8B:
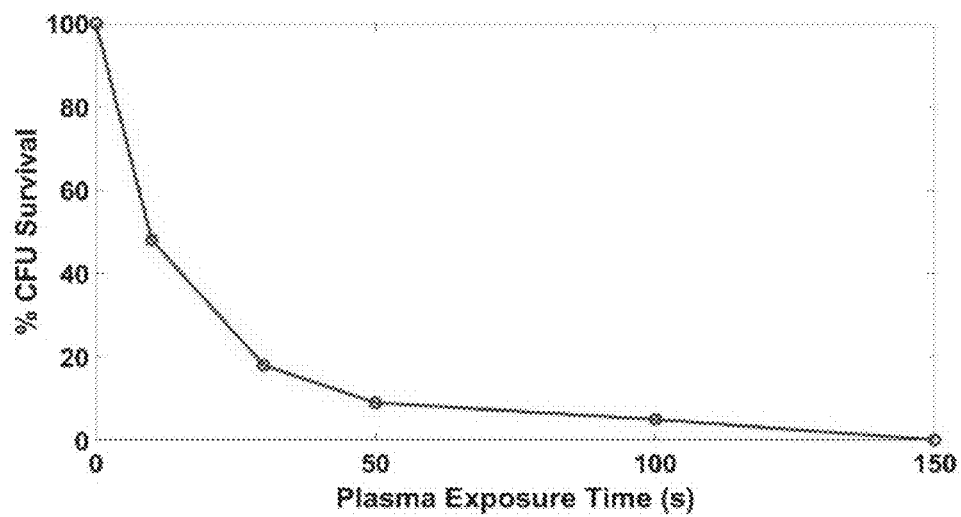

A 4-day *E. coli* (0157:H7) biofilm was formed on a glass coverslip. Coverslips were then rinsed to remove loose cells, and the biofilm was lightly stained with 0.2% Trypan blue. This biofilm was then plasma etched using a mixture of Ar (10 slm)/$O_2$ (0.5 slm) at a gap of 1 mm and an AC voltage of 4.5 kV at 20 kHz. A channel was etched through the biofilm to the glass substrate below. Several similar experiments with different exposure times and gas flow rates were performed showing very similar results. After plasma etch for 45 s, the sample was imaged to show the channel as in FIG. 8A. The etched channel in the biofilm is clearly indicated. Then a stylus profilometer was used to measure the biofilm thickness and etch channel. This result indicates that the biofilm is completely removed down to the glass. In another series of experiments, the Ar/$O_2$ plasma was used to treat the whole surface of unstained 2-day *Staph. aureus* biofilms grown on glass coverslips. The coverslip containing the biofilm was placed on a rotating platform 0.5 cm below the device and exposed to Ar/$O_2$ plasma to treat the entire biofilm. Following plasma treatment (0-150 sec), the biofilm was disaggregated from the coverslip by vigorous vortexing with 0.5 mm glass beads, and the liberated surviving colony forming units (CFU) determined based on standard plate counts. A comparison of biofilm quantity by crystal violet staining of coverslips before and after vortexing indicated that >95% of the biofilm was removed from the coverslip by this procedure (data not shown). A plot of the average CFU counts versus plasma exposure time (replicate experiments) is shown in FIG. 8B. As can be seen, the plasma treatment caused a 50% reduction in viable CFU for every 10 s of exposure, and a 3-log reduction in viable CFU in <1.50 s of exposure. This preliminary result demonstrates the plasma system can debride stained biofilm as proposed. Note that all biofilm was stained but that the plasma also etches unstained biofilm.

The disclosure being thus described, it will be obvious that the same may be varied in many ways. Such variations are not to be regarded as a departure from the spirit and scope of the disclosure and all such modifications are intended to be included within the scope of the following claims.

What is claimed is:

1. A plasma scalpel system comprising:
   at least one plasma scalpel dynamically controlled by a computer control system, wherein the computer control system controls (i) movement of the plasma scalpel in three dimensions with high spatial precision; and (ii) a variable biofilm etch rate in real time using system operating parameters;
   a biofilm imaging system that marks a biofilm in a wound and/or necrotic tissue and provides a spatial location of the biofilm to the computer control system, wherein the biofilm imaging system marks the biofilm and/or the necrotic tissue by staining the biofilm and/or necrotic tissue; flushes the wound where the biofilm is located to remove excess stain; and illuminates the wound with visible light and a camera or fiber optic system; and
   a biofilm detritus removal system that removes bacteria and byproducts of a biofilm destroyed by the plasma scalpel.

2. The system of claim 1, wherein the plasma scalpel comprises a discharge formed using at least two insulated electrodes spaced horizontally apart.

3. The system of claim 1, further comprising at least one additional dynamically controlled plasma scalpel.

4. The system of claim 1, further comprising an array of dynamically controlled plasma scalpels.

5. The system of claim 1, wherein the biofilm imaging system comprises scanning laser tomography.

6. The system of claim 1, wherein the computer control system applies control features of electrode spacing, DC electrode area, channel diameter, gas ratio, gas flow rate, capacitive discharge power, DC electrode voltage, scalpel to wound distance, relative bias, angle of incidence, three-dimensional positioning stage, multidimensional positioning stage, and/or combinations thereof.

7. The system of claim 1, wherein a plasma source is dynamically controlled in real-time with a response time less than 500 milliseconds.

8. The system of claim 1, wherein the three-dimensional scalpel positioning stage will position the scalpel from about 0.01 mm to about 20 mm above the biofilm and move the scalpel as needed to debride the wound.

9. The system of claim 1, wherein a three-dimensional scalpel positioning stage of the computer control system positions the scalpel at less than 5 mm above the biofilm and moves the scalpel as needed to debride the wound.

10. The system of claim 1, wherein a three-dimensional scalpel positioning stage of the computer control system rasters the scalpel to remove the biofilm.

11. The system of claim 1, wherein the biofilm detritus removal system comprises a slightly negative pressure and/or vacuum tube adjacent to the plasma source.

12. The system of claim 1, wherein the removal system comprises a flexible chamber with cushions that rest against the body to provide a limited seal around the wound.

13. A method of treating wounds comprising:
provide the plasma scalpel system according to claim 1; and
debriding the wound using the plasma scalpel system.

14. The method of claim 13, wherein treatment time is less than about 60 minutes.

15. The method of claim 13, wherein treatment time is less than about 30 minutes.

16. A method of selectively removing biofilm comprising:
identifying and staining the biofilm;
employing the plasma scalpel system according to claim 1; and
removing the biofilm.

17. The method according to claim 15, wherein the treatment time is less than about 60 minutes.

18. The method according to claim 15, wherein the treatment time is less than about 30 minutes.

19. The method according to claim 15, wherein the biofilm is removed via a slightly negative pressure and/or vacuum tube.

* * * * *